United States Patent
Ueda (10) Patent No.: US 10,610,321 B2
(45) Date of Patent: Apr. 7, 2020

(54) DRAPE, SURGICAL MICROSCOPE, AND SURGICAL MICROSCOPE SYSTEM

(71) Applicant: Sony Olympus Medical Solutions Inc., Tokyo (JP)

(72) Inventor: Masaaki Ueda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/904,550

(22) Filed: Feb. 26, 2018

(65) Prior Publication Data

US 2018/0280101 A1 Oct. 4, 2018

(30) Foreign Application Priority Data

Mar. 29, 2017 (JP) .................. 2017-064843

(51) Int. Cl.
*A61B 46/10* (2016.01)
*A61B 90/20* (2016.01)
*G02B 21/00* (2006.01)
*A61B 17/00* (2006.01)

(52) U.S. Cl.
CPC .............. *A61B 46/10* (2016.02); *A61B 90/20* (2016.02); *A61B 2017/00902* (2013.01); *G02B 21/0012* (2013.01)

(58) Field of Classification Search
CPC .......... A61B 46/10; A61B 2017/00902; A61B 90/20; G02B 21/0012
See application file for complete search history.

(56) References Cited

U.S. PATENT DOCUMENTS

| | | | | | |
|---|---|---|---|---|---|
| 3,528,720 | A | * | 9/1970 | Treace | A61B 46/10 359/510 |
| 3,698,791 | A | * | 10/1972 | Walchle | G02B 7/001 359/510 |
| 4,045,118 | A | * | 8/1977 | Geraci | G02B 23/18 359/510 |
| 4,051,845 | A | * | 10/1977 | Collins | A61B 46/23 128/855 |
| 4,799,779 | A | * | 1/1989 | Mesmer | G02B 21/0012 206/305 |
| 4,887,615 | A | * | 12/1989 | Taylor | A61B 1/00142 128/850 |
| 5,301,657 | A | * | 4/1994 | Lafferty | A61B 1/00096 206/438 |
| 5,591,119 | A | * | 1/1997 | Adair | A61B 1/00126 396/17 |
| 5,792,045 | A | * | 8/1998 | Adair | A61B 1/042 600/122 |

(Continued)

FOREIGN PATENT DOCUMENTS

JP 2003-220077 8/2003

*Primary Examiner* — William R Alexander
*Assistant Examiner* — Balram T Parbadia
(74) *Attorney, Agent, or Firm* — Xsensus LLP (57) ABSTRACT

A drape maintains a sterile state of a surgical microscope by covering the surgical microscope that enlarges and observes a minute portion of an observation object, and includes: a main body portion that is folded in an unused state and expanded in an in-use state to cover the surgical microscope; and a handle portion that promotes a state change of the drape from the unused state to the in-use state.

12 Claims, 8 Drawing Sheets

(56) References Cited

U.S. PATENT DOCUMENTS

| | | | | |
|---|---|---|---|---|
| 6,158,801 A | * | 12/2000 | Tucker | B60J 5/0487 296/146.1 |
| 6,497,233 B1 | * | 12/2002 | DeAngelis | A61B 50/13 128/849 |
| 2002/0151848 A1 | * | 10/2002 | Capote, Jr. | A61B 46/10 604/171 |
| 2004/0127891 A1 | * | 7/2004 | Humble | A61B 1/00142 606/1 |
| 2010/0275929 A1 | * | 11/2010 | Kaska | A61B 46/00 128/852 |
| 2015/0366618 A1 | * | 12/2015 | Higuchi | A61B 90/50 359/510 |
| 2015/0374445 A1 | * | 12/2015 | Gombert | B25J 15/0206 606/130 |

* cited by examiner

DRAPE, SURGICAL MICROSCOPE, AND SURGICAL MICROSCOPE SYSTEM

CROSS-REFERENCE TO RELATED APPLICATION

The present application claims priority to and incorporates by reference the entire contents of Japanese Patent Application No. 2017-064843 filed in Japan on Mar. 29, 2017.

BACKGROUND

The present disclosure relates to a drape, a surgical microscope, and a surgical microscope system.

In a surgical microscope equipped with a microscope unit that observes a minute portion in a brain or the like of a patient as an observation object and an arm that movably supports the microscope unit, a drape is used to maintain a sterile state. The drape is a bag-like member made of a material such as vinyl and is attached so as to cover the microscope unit and the arm (for example, refer to JP 2003-220077 A).

SUMMARY

In the surgical microscope described in JP 2003-220077 A, a plurality of eyepieces are provided for a plurality of persons to perform simultaneous observation. Therefore, when attaching the drape, it is necessary to pass through an eyepiece portion having a complicated shape; therefore, it is difficult to say that attachment of the drape is easy.

There is a need for a drape, an surgical microscope, and a surgical microscope system that may be easily attached to a surgical microscope.

A drape according to one aspect of the present disclosure may maintain a sterile state of a surgical microscope by covering the surgical microscope that enlarges and observes a minute portion of an observation object, and include: a main body portion that is folded in an unused state and expanded in an in-use state to cover the surgical microscope; and a handle portion that promotes a state change of the drape from the unused state to the in-use state.

DETAILED DESCRIPTION

Hereinafter, embodiments of the present disclosure will be described with reference to the accompanying drawings. In the description of the drawings, the same reference numerals are attached to the same parts. It should be noted that the drawings are schematic, and sizes of the same portions and ratios of sizes between the same portions in the drawings may be different in some cases.

First Embodiment

Figure 1:
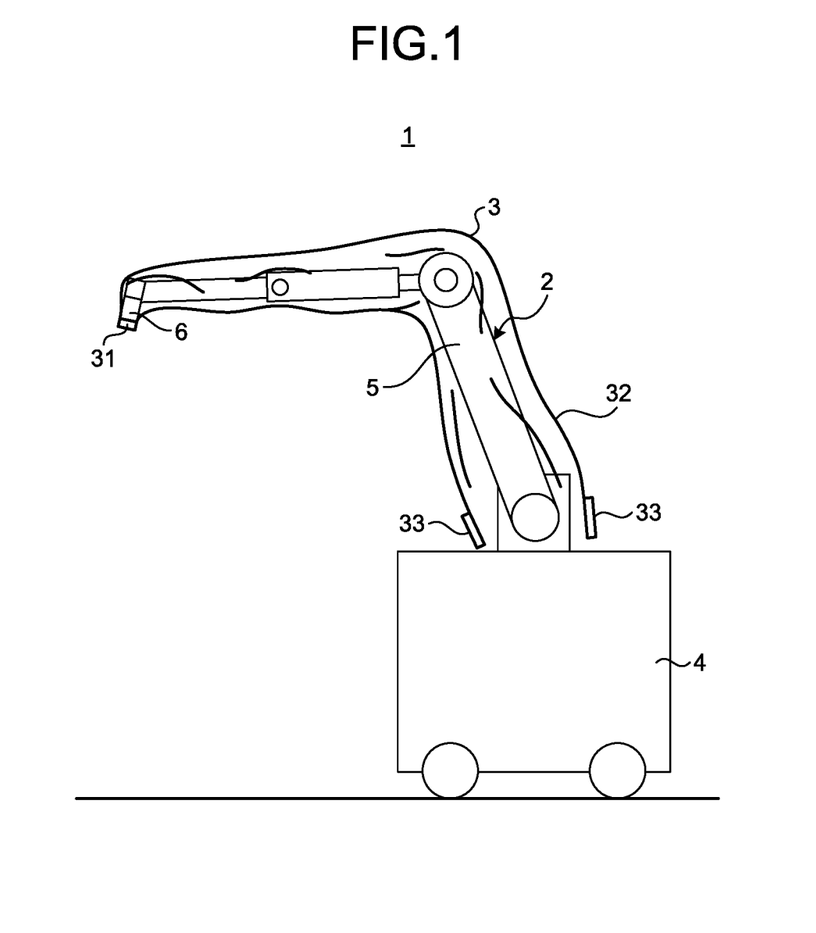
FIG. 1 is a view illustrating a configuration of a surgical microscope system according to a first embodiment.

FIG. 1 is a view illustrating a configuration of a surgical microscope system according to a first embodiment. A surgical microscope system 1 illustrated in FIG. 1 includes a surgical microscope 2, and a drape 3 that covers a part including a distal end portion of the surgical microscope 2 and maintains a sterile state of the surgical microscope 2.

The surgical microscope 2 has a function as a microscope for enlarging and capturing the microstructure of an observation object. The surgical microscope 2 includes a base portion 4 that is movable on a floor surface and in which a control circuit of the surgical microscope 2 is provided, a support portion 5 having a plurality of sets each including two arm portions and a joint portion that rotatably connects one of the two arm portions to the other, the support portion 5 being supported by the base portion 4, and a columnar microscope unit 6 that is provided at a distal end of the support portion 5 and enlarges and captures a minute portion of an observation object.

Figure 2:
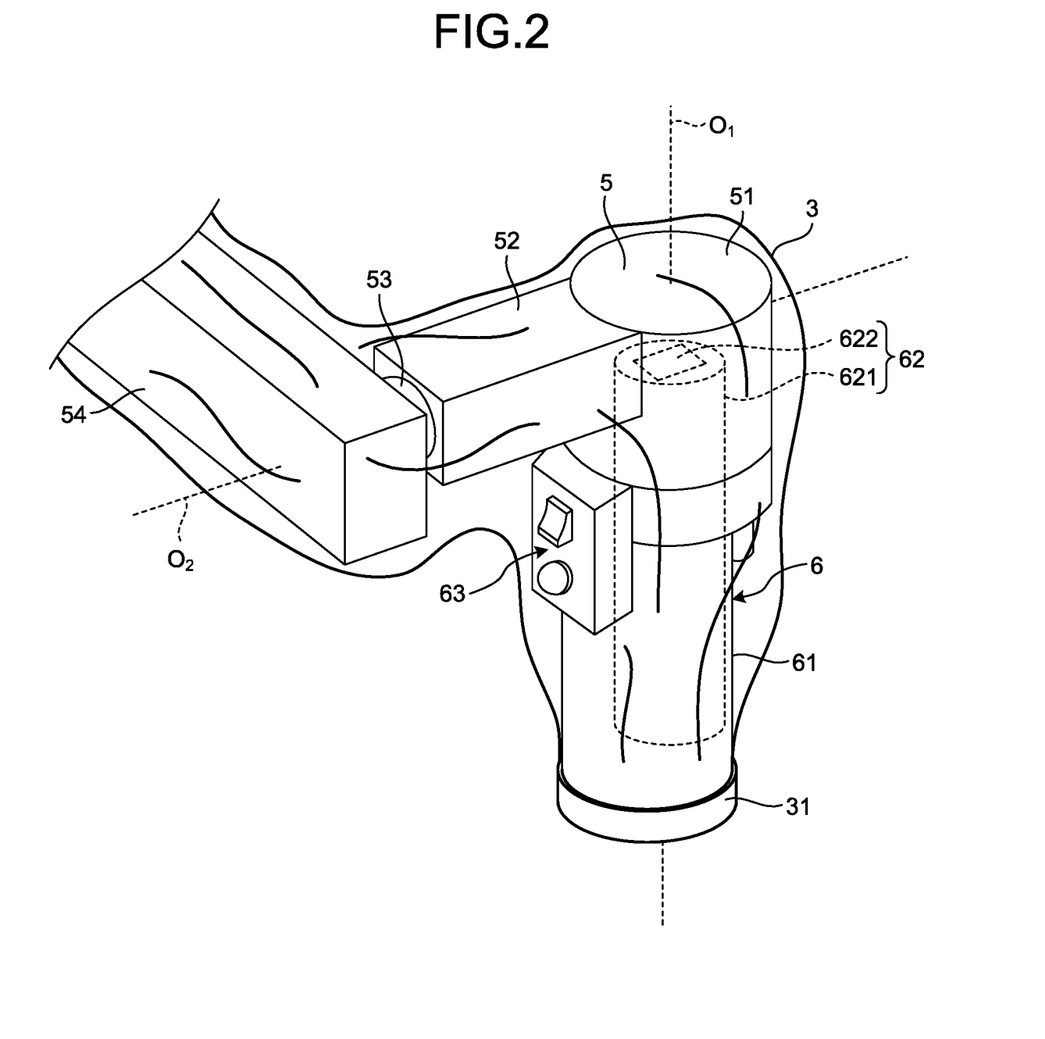
FIG. 2 is an enlarged perspective view illustrating a configuration of a drape to be attached to a distal end portion of a surgical microscope and a configuration of a support portion and a microscope unit at a distal end portion of a surgical microscope.

FIG. 2 is an enlarged perspective view illustrating a configuration of the drape 3 to be attached to a distal end portion of the surgical microscope 2 and a configuration of the support portion 5 and the microscope unit 6 at the distal end portion of the surgical microscope 2.

First, the configuration of the distal end portion of the support portion 5 will be described. The support portion 5 includes a first joint portion 51 that rotatably supports the microscope unit 6 on the distal end side, a first arm portion 52 fixed to the first joint portion 51 and extending from a side surface of the first joint portion 51, a second joint portion 53 that rotatably holds the first arm portion 52 on the distal end side, and a second arm portion 54 whose distal end portion is fixed to the second joint portion 53.

The first joint portion 51 has a cylindrical shape and holds the microscope unit 6 so as to be rotatable around a first axis $O_1$ which is a center axis in a height direction. The first arm portion 52 has a shape extending in a direction orthogonal to the first axis $O_1$ from a side surface of the first joint portion 51. The second joint portion 53 has a cylindrical shape and holds the first arm portion 52 rotatably about a second axis $O_2$ which is a center axis in the height direction and orthogonal to the first axis $O_1$. The second arm portion 54 has a shape extending in a direction orthogonal to the second axis $O_2$.

A plurality of joint portions and arm portions are provided at a portion from the proximal end side of the second arm portion 54 to the base portion 4 (see FIG. 1). It is sufficient that the support portion 5 has at least one set including two arm portions and a joint portion that rotatably connects one of the two arm portions to the other. Therefore, the configuration of a part from the proximal end side of the second arm portion 54 to the base portion 4 may be appropriately changed.

The first joint portion 51 and the second joint portion 53 have electromagnetic brakes which prohibit each rotation of the microscope unit 6 and the first arm portion 52. Each electromagnetic brake is released in response to an operation input of an operation input unit (described later) provided in the microscope unit 6, and the rotation of the microscope unit 6 and the first arm portion 52 is permitted. An air brake may be applied instead of the electromagnetic brake.

The support portion 5 is formed with a hollow portion capable of accommodating a plurality of cables. Therefore, it is possible to prevent a person and an object from being caught on the cable without exposing the cable to the outside of the surgical microscope 2. Moreover, the support portion 5 may be made smaller than pulling out a plurality of cables outside the main body, which does not hinder the field of vision of a user such as an operator.

Next, the configuration of the microscope unit 6 will be described. The microscope unit 6 includes a tubular portion 61 having a cylindrical shape, an imaging unit 62 that is provided in a hollow portion of the tubular portion 61 and captures an image by enlarging an image of the observation object, and an operation input unit 63 that receives various operation inputs of the microscope unit 6.

The tubular portion 61 has a cylindrical shape with a smaller diameter than the first joint portion 51, and a cover glass for protecting the imaging unit 62 (not illustrated) is provided on an aperture surface of a lower end portion. The tubular portion 61 may be gripped by a user and has a function as a grip portion moved by the user when changing the field of view of the imaging unit 62. The shape of the tubular portion 61 is not limited to a cylindrical shape, and may be a polygonal cylindrical shape.

The imaging unit 62 includes an optical system 621 that has a plurality of lenses arranged so that an optical axis coincides with the first axis $O_1$ and that collects and forms light from an observation object, and an imaging element 622 that generates an imaging signal by receiving the light collected by the optical system 621 and performing photoelectric conversion. The imaging unit 62 enters a hollow portion of the first joint portion 51. In FIG. 2, the optical system 621 and the imaging element 622 installed in the hollow portion of the tubular portion 61 and the first joint portion 51 are schematically illustrated by broken lines.

The optical system 621 has a plurality of lenses, and may change the enlargement magnification of an observation target image and a focal length to the observation object based on a signal output from the operation input unit 63.

The imaging element 622 is configured using a charge coupled device (CCD) or complementary metal oxide semiconductor (CMOS). The imaging signal output from the imaging element 622 is transmitted to a control circuit provided inside the base portion 4 via a transmission cable provided in the internal space of the support portion 5.

The operation input unit 63 receives an input of a signal that cancels an electromagnetic brake at the first joint portion 51 and the second joint portion 53 and allows rotation of each joint portion, or an input of a signal that instructs to change the enlargement magnification in the imaging unit 62 and the focal length to an observation object. A user operates the microscope unit 6 while facing the side surface of the side surfaces of the tubular portion 61, the side surface being opposite to the side surface on which the operation input unit 63 is provided.

Next, the configuration of the drape 3 will be described. The drape 3 covers from the distal end portion of the surgical microscope 2 to the vicinity of the proximal end portion of the support portion 5 to maintain the sterile state of the portion. The main body of the drape 3 is made of a transparent and flexible material such as vinyl and has a bag shape adapted to the shape of the surgical microscope 2.

Figure 3:
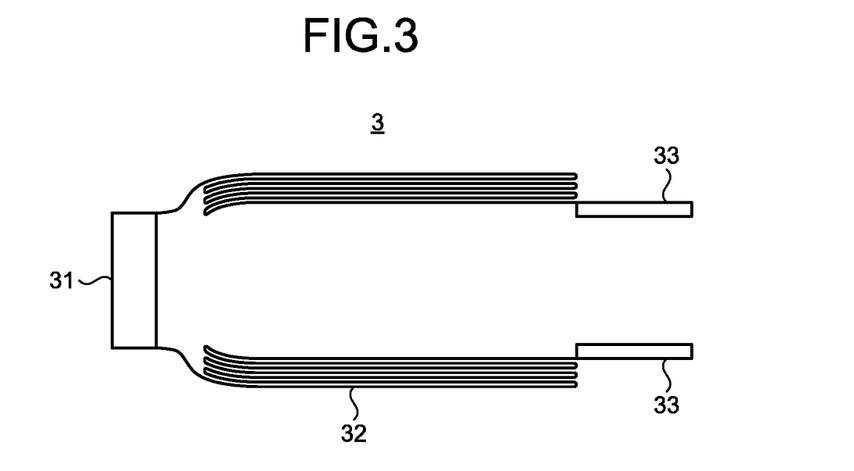
FIG. 3 is a partial cross-sectional view illustrating a configuration in a state where the drape according to the first embodiment is not in use.
Figure 4:
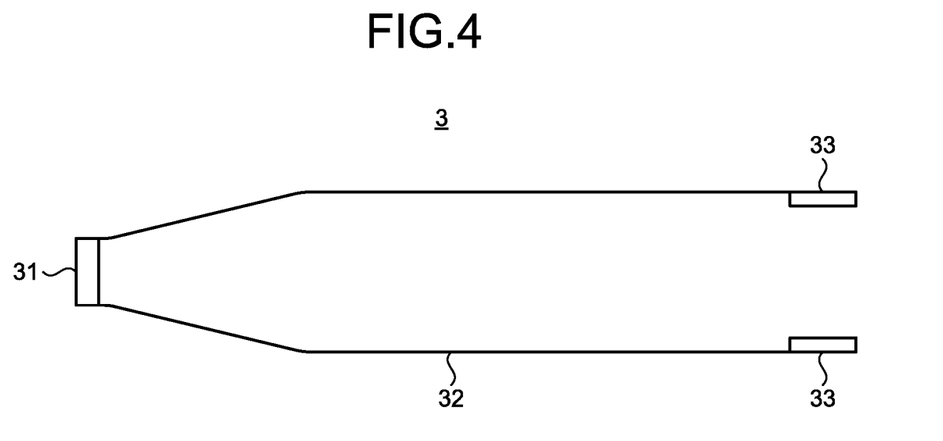
FIG. 4 is a cross-sectional view illustrating a state where a main body portion of the drape according to the first embodiment is expanded.

FIG. 3 is a partial cross-sectional view illustrating a configuration in a state where the drape 3 is not in use. FIG. 4 is a cross-sectional view illustrating a state where a main body portion 32 of the drape 3 is expanded. The drape 3 includes a cylindrical aperture cover 31 that is attached to the distal end of the tubular portion 61 of the microscope unit 6 and provided with a cover glass (not illustrated) that protects the aperture surface for collecting light from the observation object, a main body portion 32 that is folded in a state of being overlapped with the inner peripheral side in a thickness direction (vertical direction in FIG. 3) in an unused state and is expanded in an in-use state to cover the surgical microscope 2, and a strip-like drawer member 33 that is provided at an open end portion in a longitudinal direction of the main body portion 32 (left and right direction in FIG. 3), and may apply force for drawing the folded portion of the main body portion 32 from the aperture end portion along the longitudinal direction. The aperture cover 31 is provided in the main body portion 32 in a state where the aperture cover 31 may be attached to the tubular portion 61 in a state where the main body portion 32 is folded.

As illustrated in FIG. 4, the width of the main body portion 32 in a direction perpendicular to a longitudinal direction (the length in the vertical direction in FIG. 4) monotonically increases from an end portion on a side where the aperture cover 31 is provided to the aperture end portion along the longitudinal direction. As used herein, the term "monotonically increasing in width" includes a case where the width of a part is uniform from the end portion on the side where the aperture cover 31 is provided to the aperture end portion along the longitudinal direction, as illustrated in FIG. 4. In FIGS. 3 and 4, two drawer members 33 are illustrated; however, the number of drawer members 33 provided at the aperture end portion may be appropriately changed. The main body portion 32 is made of a transparent and flexible material such as vinyl. The main body portion 32 may have a tubular shape having the same width along the longitudinal direction.

The drawer member 33 is provided at the aperture end portion in the longitudinal direction of the main body portion 32 and has a function as a handle portion that promotes a state change of the drape 3 from an unused state to an in-use state. Note that it is also possible to apply a member such as a handle as a drawer member.

Figure 5:
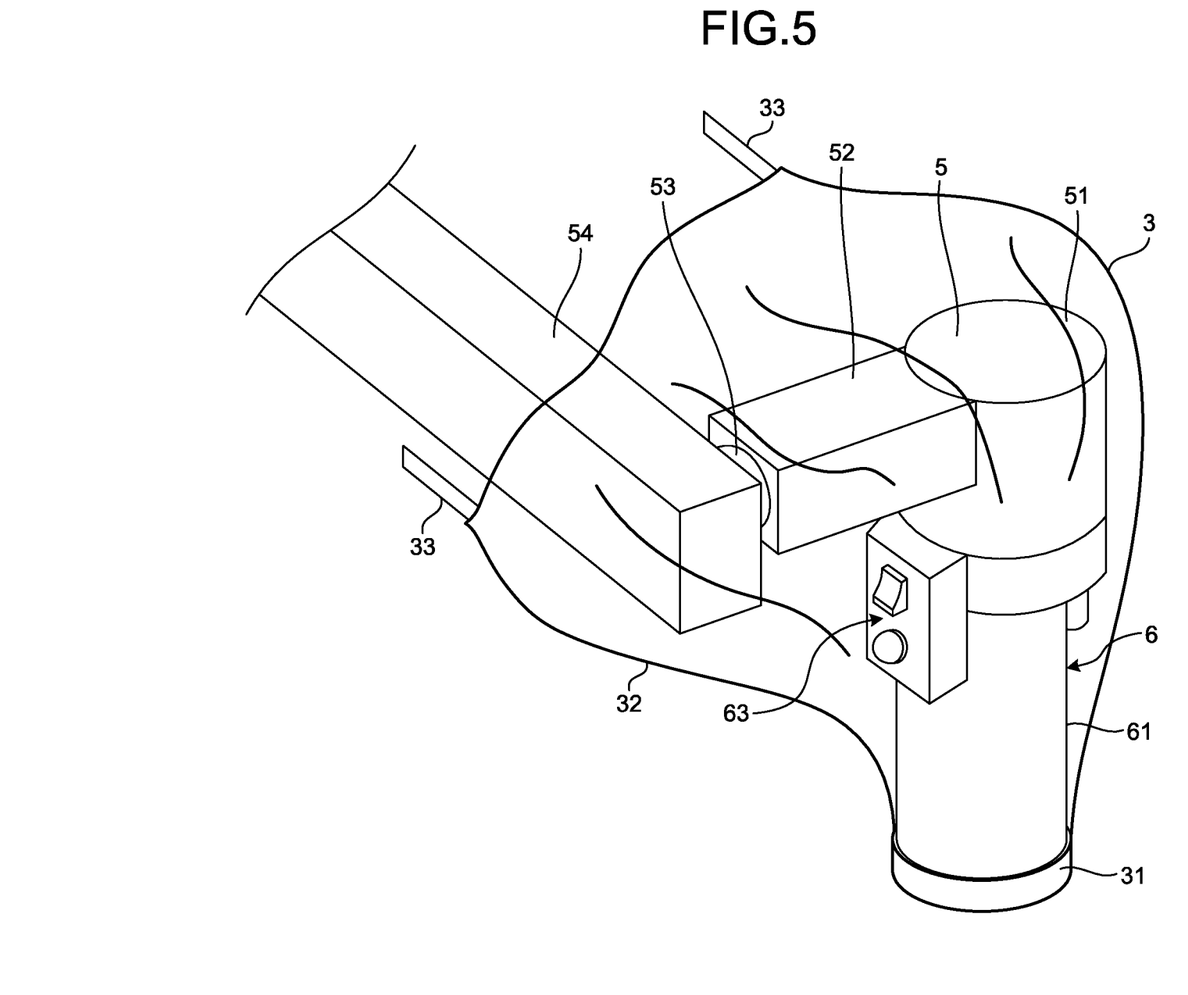
FIG. 5 is a view illustrating a state where a distal end portion of the surgical microscope is covered while the main body portion of the drape according to the first embodiment is not expanded.

A method of attaching the drape 3 having the above configuration to the surgical microscope 2 will be described. First, after a user inserts the microscope unit 6 into the hollow portion of the drape 3 in the unused state, attaches the aperture cover 31 to the distal end of the tubular portion 61, and then the distal end portion of the surgical microscope 2 is covered without expanding the main body portion 32 of the drape 3. FIG. 5 is a view illustrating a state where the distal end portion of the surgical microscope 2 is covered while the main body portion 32 is not expanded. In the state illustrated in FIG. 5, the main body portion 32 is in a state of being folded. Thereafter, the user grasps the drawer member 33 by hand and pulls the support portion 5 along the extending direction to the proximal end side, thereby expanding the main body portion 32 to the vicinity of the proximal end portion of the support portion 5.

Figure 6:
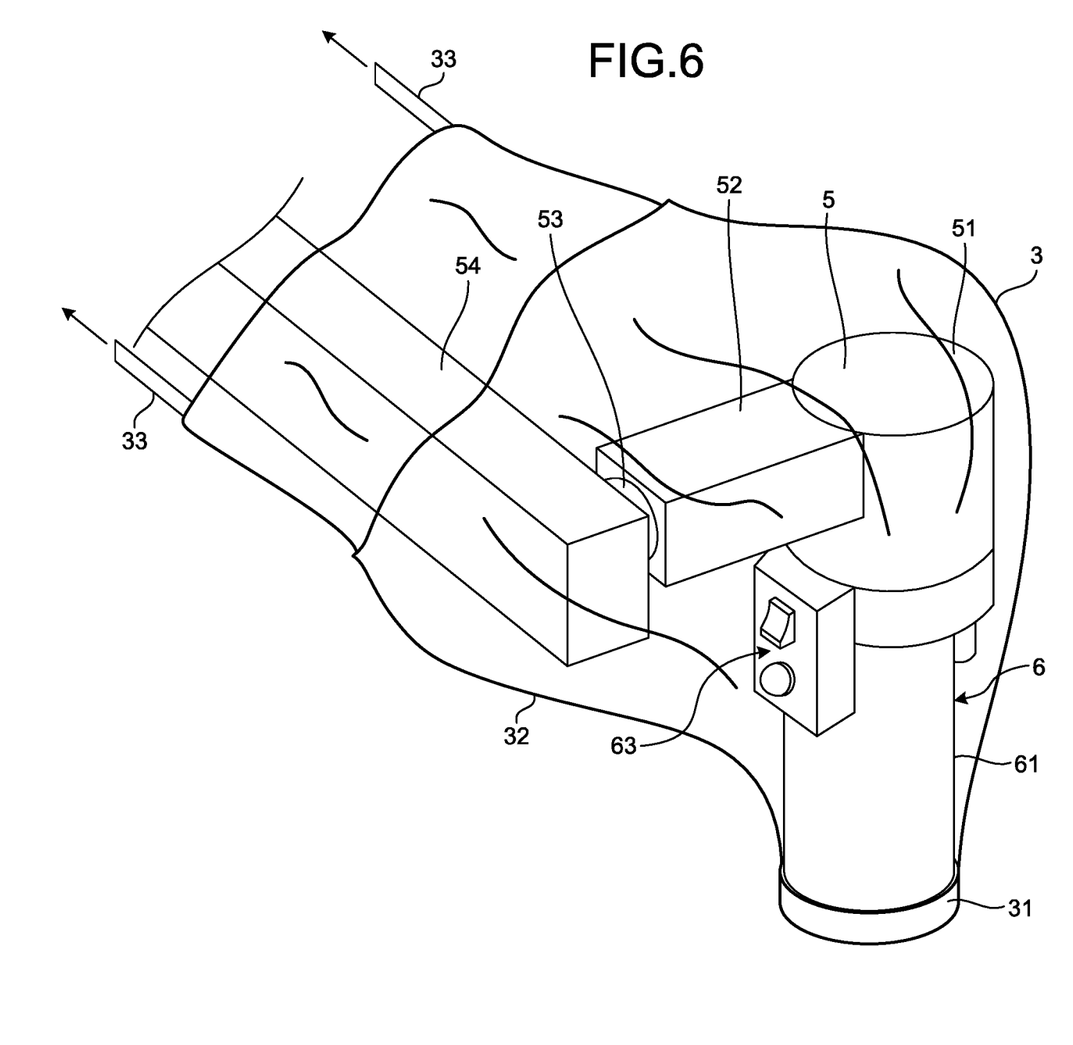
FIG. 6 is a view illustrating a situation in which a folded portion of the main body portion of the drape according to the first embodiment has begun to expand.
Figure 7:
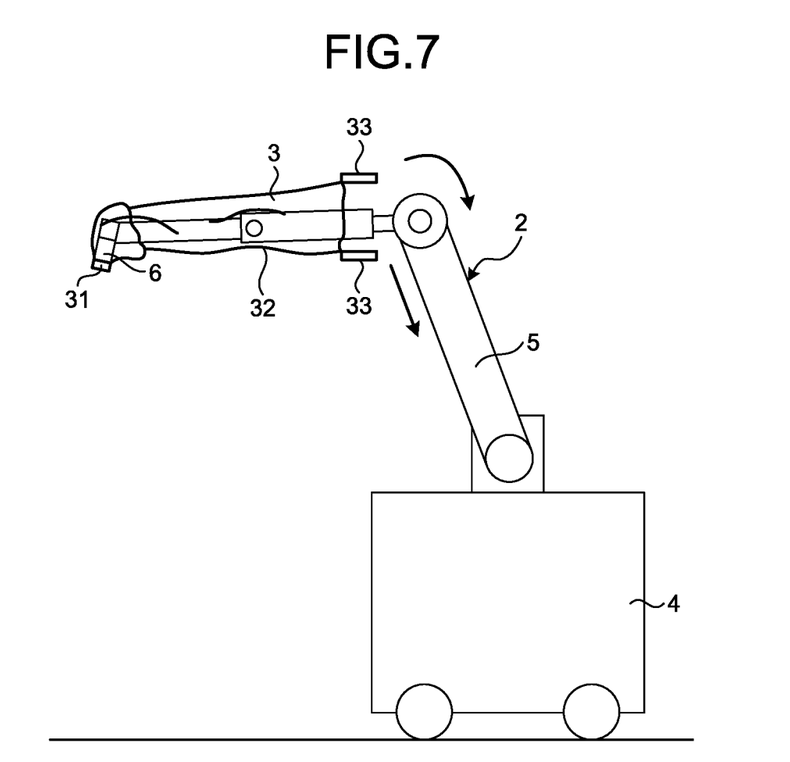
FIG. 7 is a view illustrating a situation in the course of expanding the main body portion of the drape according to the first embodiment.

FIG. 6 is a view illustrating a situation in which the drawer member 33 is pulled to start expanding the folded portion of the main body portion 32. Further, FIG. 7 is a view illustrating a state where the main body portion 32 is further expanded from the state illustrated in FIG. 6. Arrows illustrated in FIGS. 6 and 7 indicate the direction in which the drawer member 33 is pulled. As the drawer member 33 is pulled to the vicinity of the proximal end portion of the support portion 5, the main body portion 32 covers substantially the entire surface of the support portion 5, as illustrated in FIG. 1. After reaching the state illustrated in FIG. 1, the drape 3 may be fixed to the support portion 5 by winding a member such as a string from above the drape 3 at an appropriate position of the arm portion of the support portion 5.

According to the first embodiment described above, since the drawer member 33 as a handle portion that promotes a state change from the unused state to the in-use state of covering the surgical microscope 2 is provided at the aperture end portion of the main body portion 32 of the drape 3 which is folded toward the inner peripheral side in the thickness direction in the unused state, attachment of the drape 3 to the surgical microscope 2 is easy. As a result, surgical preparation may be performed efficiently.

Furthermore, according to the first embodiment, since the drape 3 is folded toward the inner peripheral side of a bag in the unused state, there is no possibility that the drape 3 will be expanded in the longitudinal direction before being attached to the surgical microscope 2 and thus easy handling may be achieved in the unused state. Therefore, it is possible to prevent a situation where a user unexpectedly expands the drape 3 and inevitably has to forcibly abandon the drape 3 in contact with a filthy place, so that the waste of the drape 3 may be reduced.

Furthermore, according to the first embodiment, the surgical microscope 2 having a simple shape includes the imaging unit 62 that enlarges and captures a minute portion of the observation object, and a grip portion (tubular portion 61) that has a tubular shape that may be gripped by a user and accommodates the imaging unit in the hollow portion; therefore, a shape when the main body portion 32 of the drape 3 is expanded may be formed to a shape in which the width in the direction orthogonal to the longitudinal direction monotonically increases from the end portion on the side where the aperture cover 31 is provided along the longitudinal direction to the aperture end portion. In this sense as well, attachment of the drape 3 to the surgical microscope 2 is easy.

Here, the effect of the first embodiment will be described as compared with JP 2003-220077 A described above. In JP 2003-220077 A, in order to prevent the generation of a large gap between the drape and the surgical microscope as a result of enlarging the drape to correspond to a surgical microscope having a complicated shape, air in the gap is sucked by a pump to reduce the gap between the drape and the surgical microscope. However, such a known configuration needs a pump, the structure becomes complicated, and the cost of the apparatus has been increased. Furthermore, since the main body portion of the drape has a large area, when the drape is bundled and fixed to the support portion of the surgical microscope by using a string or the like after reducing the gap by suction by the pump, the drape is disadvantageously in close contact with the microscope main body and the support portion in a state having a thickness, which raises a problem that the operability of the surgical microscope deteriorates. On the other hand, in the first embodiment, in addition to easy attachment of the drape 3 to the surgical microscope 2 by providing the drawer member 33, since the surgical microscope 2 has a simple shape, the shape of the drape 3 is also simple, and there is no possibility that the drape 3 affects the operability of the surgical microscope 2.

Note that instead of a configuration in which the main body portion of the drape is folded toward the inner peripheral side in the thickness direction in the unused state, the drape may be folded to the outer peripheral side in the thickness direction.

Second Embodiment

Figure 8:
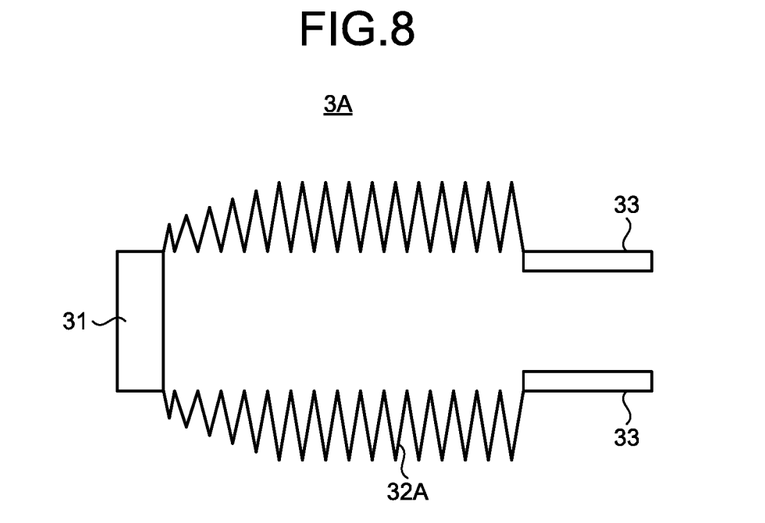
FIG. 8 is a partial cross-sectional view illustrating a configuration in a state where a drape according to a second embodiment is not in use.

FIG. 8 is a partial cross-sectional view illustrating a configuration in a state where a drape according to a second embodiment is not in use. A drape 3A illustrated in FIG. 8 includes an aperture cover 31, a main body portion 32A, and a drawer member 33. The main body portion 32A has a bellows shape folded in a longitudinal direction (left and right direction in FIG. 8) in the unused state, and is expanded by being pulled by the drawer member 33. In FIG. 8, the main body portion 32A is described as being expanded in the longitudinal direction in order to clearly indicate the bellows shape; however, in fact, the main body portion 32A is formed like a bellows folded in the longitudinal direction. Further, the shape of the drape 3A when the drawer member 33 is pulled to widen the drape 3A is the same as that of the drape 3 described in the first embodiment (see FIG. 4).

The drape 3A having the above configuration, together with the surgical microscope 2 described in the first embodiment, constitutes a surgical microscope system according to the second embodiment.

In the second embodiment, a method of expanding the drape 3A and attaching the drape 3A to the surgical microscope 2 is the same as in the first embodiment. That is, first, a user attaches the aperture cover 31 to the distal end of a tubular portion 61, covers the distal end portion of the surgical microscope 2 without expanding the drape 3A, then grasps the drawer member 33 by hand and expands the main body portion 32A to the vicinity of the proximal end portion of a support portion 5 while pulling the main body portion 32A along a direction in which the support portion 5 extends toward the proximal end side.

According to the above-described second embodiment, the drawer member 33 as a handle portion is provided at the aperture end portion of the main body portion 32A of the drape 3A folded in a bellows shape along the longitudinal direction in the unused state, attachment of the drape 3A to the surgical microscope 2 is easy.

Further, according to the second embodiment, as in the first embodiment, since preparation for surgery may be performed efficiently and a shape when the drape 3A is expanded is simple, an effect that attachment of the drape 3A to the surgical microscope 2 becomes easy is obtained.

Note that the drawer member 33 for the main body portion 32A may be provided on the outer peripheral side in the vicinity of the aperture end portion.

Modification of Second Embodiment

Figure 9:
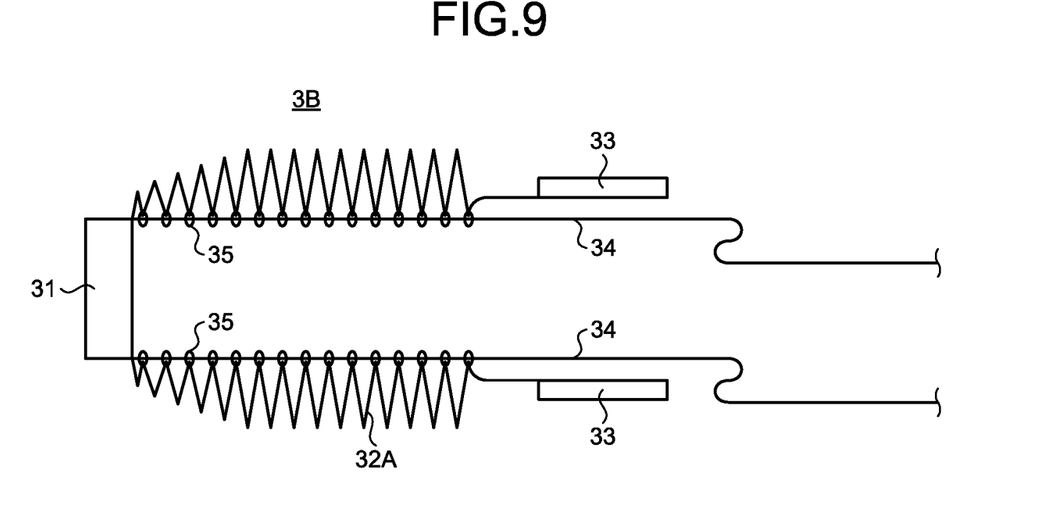
FIG. 9 is a partial cross-sectional view illustrating a configuration in a state where the drape according to a modification of the second embodiment is not in use.

FIG. 9 is a partial cross-sectional view illustrating a configuration in a state where the drape according to a modification of the second embodiment is not in use. A drape 3B illustrated in FIG. 9 includes the aperture cover 31, the main body portion 32A, the drawer member 33, a string-like guide portion 34 that extends by a length corresponding to a length from the aperture cover 31 to the proximal end portion of the support portion 5, and a plurality of ring-shaped insertion portions 35 that are provided along a longitudinal direction of the main body portion 32A in the vicinity of a fold line on the inner peripheral side of the bellows of the main body portion 32A, the guide portion 34 being inserted through each of the insertion portions 35. The insertion portion 35 is formed using the same material (vinyl or the like) as the main body portion 32A. In this modification, the guide portion 34 and the insertion portion 35 constitute a handle portion together with the drawer member 33.

In addition, also in FIG. 9, it is described in a mode in which the main body portion 32A is expanded more in the longitudinal direction than the actual direction in order to clearly indicate the bellows shape. Furthermore, although FIG. 9 illustrates two guide portions 34, the number of the guide portions 34 is not limited thereto, and may be three or more.

When attaching the drape 3B having the above configuration to the surgical microscope 2, the user inserts a microscope unit 6 into the hollow portion of the drape 3B in the unused state and attaches the aperture cover 31 to the distal end of the tubular portion 61, and then extends the guide portion 34 to the proximal end portion of the support portion 5. Subsequently, the user pulls the drawer member 33 along the guide portion 34 in a state where tension is applied to the guide portion 34, thereby expanding the main body portion 32A to the vicinity of the proximal end portion of the support portion 5.

It is a matter of course that the modification of the above-described second embodiment has the same effects as those of the second embodiment. In addition, according to this modification, the main body portion 32A expands along the guide portion 34; therefore, when attaching to the surgical microscope 2, the main body portion 32A is easily expanded further.

Third Embodiment

Figure 10:
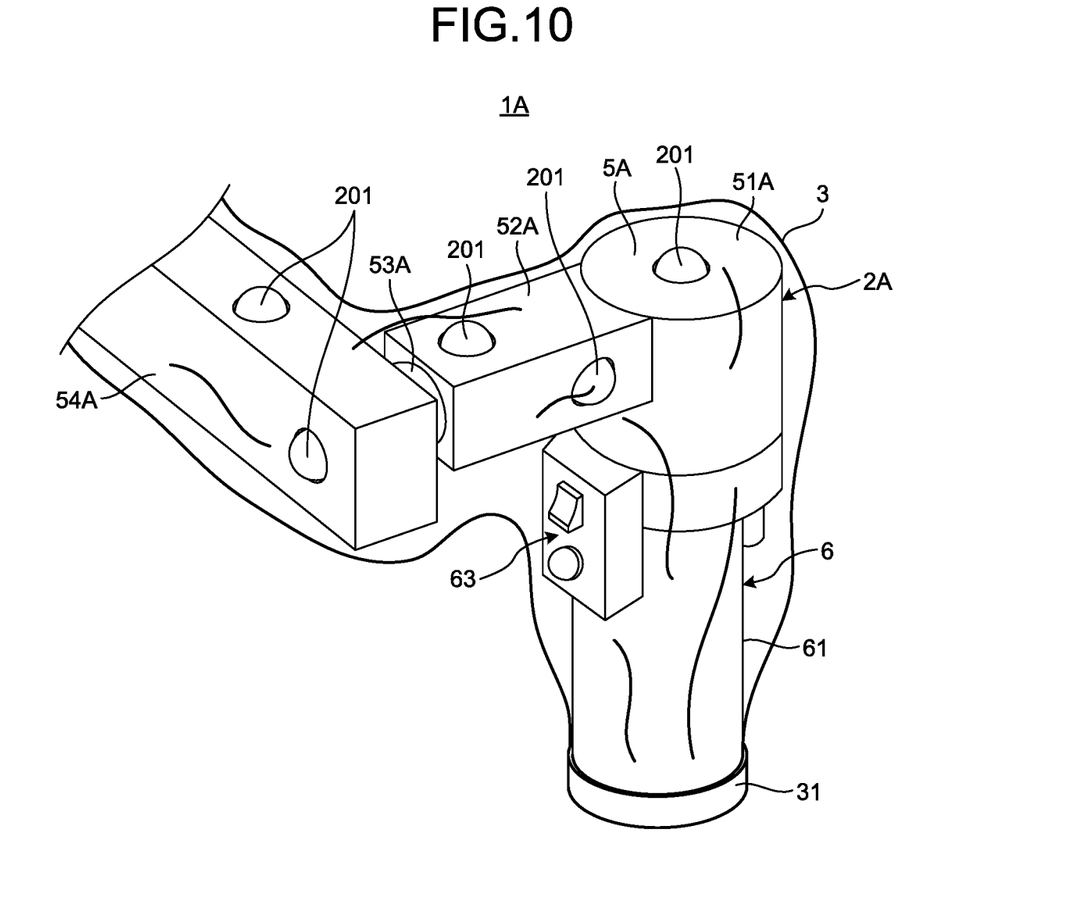
FIG. 10 is a view illustrating a configuration of a main portion of a surgical microscope system according to a third embodiment.

FIG. 10 is a view illustrating a configuration of a main portion of a surgical microscope system according to a third embodiment. A surgical microscope system 1A illustrated in FIG. 1 includes a surgical microscope 2A and a drape 3.

A support portion 5A of the surgical microscope 2A has a plurality of ball rollers 201 respectively provided on the surfaces of a first joint portion 51A, a first arm portion 52A, and a second arm portion 54A. The ball roller 201 is appropriately provided along the support portion 5A.

In the surgical microscope system 1A having the above configuration, when the main body portion 32 of the drape 3 is expanded, since the ball roller 201 that contacts a main body portion 32 rotates, the frictional force between the main body portion 32 and the support portion 5A is small. That is, the ball roller 201 is a friction reducing portion that reduces frictional force generated between the main body portion 32 and the surgical microscope 2A when the state of the drape 3 changes. Such a ball roller 201 together with the drawer member 33 constitutes a sliding portion that promotes a state change from an unused state in the drape 3 to an in-use state of covering the surgical microscope 2A.

In the third embodiment, the drape provided in the surgical microscope system does not have to include the drawer member 33. In this case, the ball roller 201 separately constitutes the sliding portion.

According to the above-described third embodiment, since the plurality of ball rollers 201 as the sliding portion are provided on the support portion 5A of the surgical microscope 2A, the frictional force between the main body portion 32 of the drape 3 and the support portion 5A is reduced, the frictional force being generated at the time of the state change, and attachment of the drape 3 to the surgical microscope 2A is facilitated. As a result, surgical preparation may be performed efficiently.

Instead of the ball roller 201, a plurality of pulleys that rotate in a direction in which the support portion 5A extends may be provided.

Further, the drape constituting the surgical microscope system according to the third embodiment is not limited to the drape 3. The above described drape 3A or 3B may be applied or a drape having a configuration in which the drawer member 33 is removed from the drape 3A or 3B may be applied.

Fourth Embodiment

Figure 11:
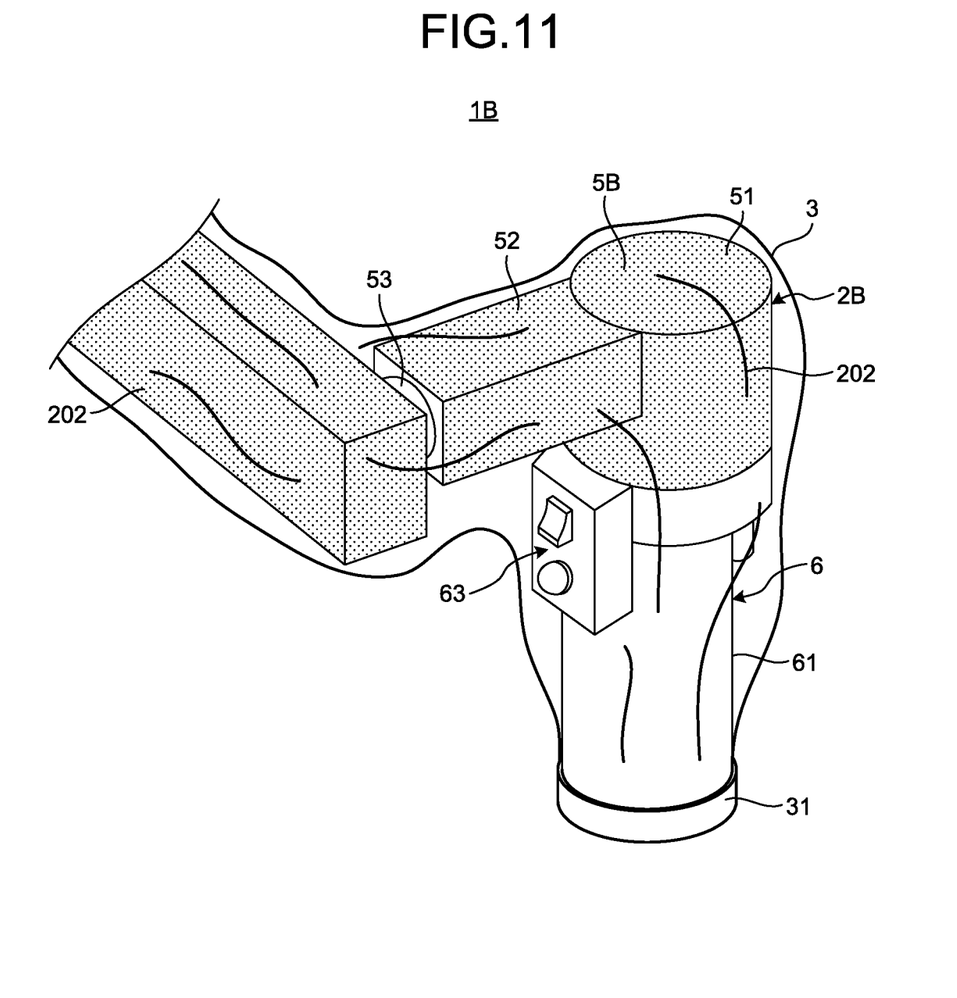
FIG. 11 is a view illustrating a configuration of a main portion of a surgical microscope system according to a fourth embodiment.

FIG. 11 is a view illustrating a configuration of a main portion of a surgical microscope system according to a fourth embodiment. A surgical microscope system 1B illustrated in FIG. 1 includes a surgical microscope 2B and a drape 3.

On the surface of a support portion 5B of the surgical microscope 2B, a lubricating portion 202 is provided. The lubricating portion 202 is formed, for example, by applying a lubricant such as fluororesin to the surface of the support portion 5B.

In the surgical microscope system 1B having the above configuration, frictional force generated between the main body portion 32 and the support portion 5B when the main body portion 32 of the drape 3 is expanded is reduced by the lubricating portion 202. That is, the lubricating portion 202 is a friction reducing portion that reduces frictional force generated between the main body portion 32 and the surgical microscope 2B when the state of the drape 3 changes. Such a lubricating portion 202 together with the drawer member 33 constitutes a sliding portion that promotes a state change from an unused state in the drape 3 to an in-use state of covering the surgical microscope 2B.

Also in the fourth embodiment, the drape provided in the surgical microscope system does not have to include the drawer member 33. In this case, the lubricating portion 202 separately constitutes the sliding portion.

According to the above-described fourth embodiment, since the lubricating portion 202 as the sliding portion formed on the surface of the support portion 5B of the surgical microscope 2B is provided, the frictional force between the main body portion 32 and the support portion 5B is reduced, the frictional force being generated at the time of the state change of the drape 3, and attachment of the drape 3 to the surgical microscope 2B is easy. As a result, surgical preparation may be performed efficiently.

Instead of providing the lubricating portion 202 on the entire surface of the support portion 5B, the lubricating portion 202 may be provided only on the surface of the support portion 5B which is complicated in shape and is likely to be caught by the drape 3 (for example, in the vicinity of each joint portion).

Furthermore, the ball roller 201 described in the third embodiment may be additionally provided to the support portion 5B, or the ball roller 201 and the lubricating portion 202 may be provided at different positions of the support portion 5B.

Further, the drape constituting the surgical microscope system according to the fourth embodiment is not limited to the drape 3 as in the third embodiment. The above described drape 3A or 3B may be applied or a drape having a configuration in which the drawer member 33 is removed from the drape 3A or 3B may be applied.

Another Embodiment

An optical surgical microscope having an eyepiece portion for allowing a user to bring his/her eyes close to observe the image of an observation object may be applied as a surgical microscope. In this case, although the shape of the drape is complicated, attachment of the drape to the surgical microscope is facilitated by providing a handle portion.

Furthermore, a base portion of the surgical microscope may be fixed to a ceiling, a wall surface, a bed, or the like instead of being provided movably on a floor surface.

Note that the following configuration also belongs to the technical scope of the present disclosure.

(1) A drape that maintains a sterile state of a surgical microscope by covering the surgical microscope that enlarges and observes a minute portion of an observation object, including: a main body portion that is folded in an unused state and expanded in an in-use state to cover the surgical microscope; and a handle portion that promotes a state change of the drape from the unused state to the in-use state.

(2) The drape according to (1), wherein the handle portion includes a drawer member that is provided at an aperture end portion of the main body portion and is capable of applying force for pulling out a folded portion of the main body portion from the aperture end portion along a longitudinal direction of the main body portion.

(3) The drape according to (1) or (2), wherein the main body portion is folded in a state of being overlapped in a thickness direction in the unused state.

(4) The drape according to (3), wherein the main body portion is folded in a state of being overlapped with an inner peripheral side in the thickness direction.

(5) The drape according to (1) or (2), wherein the main body portion is folded in a state of being overlapped in a longitudinal direction in the unused state.

(6) The drape according to (5), wherein the handle portion includes a string-like guide portion that extends from an end portion in the longitudinal direction beyond the aperture end portion, the end portion being different from the aperture end portion of the main body portion, and a plurality of insertion portions that are provided along the longitudinal direction, the guide portion being inserted through each of the insertion portions.

(7) The drape according to any one of (1) to (6), wherein in a state where the main body portion is expanded, a width in a direction orthogonal to a longitudinal direction monotonically increases from an end portion in the longitudinal direction toward an aperture end portion, the end portion being different from the aperture end portion of the main body portion.

(8) The drape according to any one of (1) to (7), including an aperture cover attached to a lens barrel portion of the surgical microscope, the aperture cover being configured to protect an aperture surface, wherein the aperture cover is attachable to the lens barrel portion in a state where the main body portion is folded.

(9) A surgical microscope that enlarges and observes a minute portion of an observation object, including: a sliding portion that promotes a state change from an unused state to an in-use state in a drape including a main body portion that is folded in the unused state and is expanded in the in-use state to cover the surgical microscope, the drape being configured to maintain a sterile state of the surgical microscope.

(10) The surgical microscope according to (9), wherein the sliding portion includes a friction reducing portion that is provided in the surgical microscope and reduces frictional force generated between the main body portion and the surgical microscope when a state of the drape changes.

(11) The surgical microscope according to (9) or (10), including: an imaging unit that enlarges and captures a minute portion of an observation object; and a grip portion that has a tubular shape capable of being gripped by a user and accommodates the imaging unit in a hollow portion.

(12) A surgical microscope system including: a surgical microscope that enlarges and observes a minute portion of an observation object; and a drape that includes a main body portion that is folded in an unused state and expanded in an in-use state to cover the surgical microscope, the drape being configured to maintain a sterile state of the surgical microscope; wherein the surgical microscope includes a sliding portion that promotes a state change from the unused state to the in-use state in the drape, and the drape includes a main body portion that is folded in the unused state and expanded in the in-use state to cover the surgical microscope, and a handle portion that promotes a state change of the drape from the unused state to the in-use state.

According to the present disclosure, there is provided a drape that may be easily attached to a surgical microscope and a surgical microscope system including the drape.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A drape that maintains a sterile state of a surgical microscope by covering the surgical microscope that enlarges and observes a minute portion of an observation object, comprising:
    a main body portion that is entirely folded in an unused state and expanded in an in-use state to cover the surgical microscope; and
    a handle portion that promotes a state change of the drape from the unused state to the in-use state, and wherein the drape is configured to be placed, in the unused state, onto a distal end of the surgical microscope and then drawn over the surgical microscope, expanding a main body portion of the drape to a proximal end of the surgical microscope.

2. The drape according to claim 1, wherein
    the handle portion includes a drawer member that is provided at an aperture end portion of the main body portion and is capable of applying force for pulling out a folded portion of the main body portion from the aperture end portion along a longitudinal direction of the main body portion.

3. The drape according to claim 1, wherein the main body portion is folded in a state of being overlapped in a thickness direction in the unused state.

4. The drape according to claim 3, wherein the main body portion is folded in a state of being overlapped with an inner peripheral side in the thickness direction.

5. The drape according to claim 1, wherein the main body portion is folded in a state of being overlapped in a longitudinal direction in the unused state.

6. The drape according to claim 5, wherein the handle portion includes
   a string-like guide portion that extends from an end portion in the longitudinal direction beyond the aperture end portion, the end portion being different from an aperture end portion of the main body portion, and
   a plurality of insertion portions that are provided along the longitudinal direction, the guide portion being inserted through each of the insertion portions.

7. The drape according to claim 1, wherein in a state where the main body portion is expanded, a width in a direction orthogonal to a longitudinal direction monotonically increases from an end portion in the longitudinal direction toward an aperture end portion, the end portion being different from an aperture end portion of the main body portion.

8. The drape according to claim 1, comprising an aperture cover attached to a lens barrel portion of the surgical microscope, the aperture cover being configured to protect an aperture surface, wherein
   the aperture cover is attachable to the lens barrel portion in a state where the main body portion is folded.

9. A surgical microscope that enlarges and observes a minute portion of an observation object, comprising:
   a sliding portion that promotes a state change from an unused state to an in-use state in a drape including a main body portion that is entirely folded in the unused state and is expanded in the in-use state to cover the surgical microscope, the drape being configured to maintain a sterile state of the surgical microscope, and
   wherein the drape is configured to be placed, in the unused state, onto a distal end of the surgical microscope and then drawn over the surgical microscope, expanding a main body portion of the drape to a proximal end of the surgical microscope.

10. The surgical microscope according to claim 9, wherein the sliding portion includes a friction reducing portion that is provided in the surgical microscope and reduces frictional force generated between the main body portion and the surgical microscope when a state of the drape changes.

11. The surgical microscope according to claim 9, comprising:
    an imaging unit that enlarges and captures a minute portion of an observation object; and
    a grip portion that has a tubular shape capable of being gripped by a user and accommodates the imaging unit in a hollow portion.

12. A surgical microscope system comprising:
    a surgical microscope that enlarges and observes a minute portion of an observation object; and
    a drape that includes a main body portion that is entirely folded in an unused state and expanded in an in-use state to cover the surgical microscope, the drape being configured to maintain a sterile state of the surgical microscope; wherein
    the surgical microscope includes a sliding portion that promotes a state change from the unused state to the in-use state in the drape,
    the drape includes a handle portion that promotes a state change of the drape from the unused state to the in-use state, and
    the drape is configured to be placed, in the unused state, onto a distal end of the surgical microscope and then drawn over the surgical microscope, expanding a main body portion of the drape to a proximal end of the surgical microscope.

* * * * *